United States Patent [19]

Taylor

[11] 4,064,145
[45] Dec. 20, 1977

[54] PRODUCTION OF TETRAHYDROFURAN
[75] Inventor: Paul D. Taylor, Corpus, Christi, Tex.
[73] Assignee: Celanese Corporation, New York, N.Y.
[21] Appl. No.: 735,982
[22] Filed: Oct. 27, 1976

Related U.S. Application Data

[62] Division of Ser. No. 623,882, Oct. 20, 1975.
[51] Int. Cl.$^2$ .......................................... C07D 307/08
[52] U.S. Cl. ................................ 260/346.11; 260/602
[58] Field of Search ............. 260/346.1 R, 602, 635 A

[56] References Cited

U.S. PATENT DOCUMENTS

| | | | |
|---|---|---|---|
| T904,021 | 11/1972 | Copelin | 260/635 A |
| 3,726,905 | 4/1973 | Coates et al. | 260/346.1 R |
| 3,859,369 | 1/1975 | Copelin | 260/346.1 R X |
| 3,919,324 | 11/1975 | Himmele et al. | 260/602 |

OTHER PUBLICATIONS

Houben-Weyl, Methoden der Organischen Chemie, vol. 6/3, (1965), p. 562.

*Primary Examiner*—Richard L. Raymond

[57] ABSTRACT

This invention provides a process for producing 4-hydroxybutanal in a yield of at least 87 percent by hydroformylation of allyl alcohol in a solvent at a temperature of about 20° C–120° C and a pressure of about 15–150 psi in the presence of a rhodium metal-phosphine complex hydroformylation catalyst. Also provided are additional processing procedures for recovering the 4-hydroxybutanal product and converting it into 1,4-butanediol and tetrahydrofuran.

1 Claim, No Drawings

PRODUCTION OF TETRAHYDROFURAN

This is a division of application Ser. No. 623,882, filed Oct. 20, 1975.

BACKGROUND OF THE INVENTION

Ethylene glycol is an important constituent of commercial polyester resins. Also of increasing importance as resin constituents are higher polyols such as 1,4-butanediol. The development of new and improved commercial processes for production of higher polyols is under active investigation.

1,4-Butanediol can be derived from tetrahydrofuran, succinic acid, maleic anhydride and other four-carbon organic species, but such methods are not economically attractive. Another method of producing 1,4-butanediol is by the reaction of formaldehyde and acetylene to form 1,4-butynediol as an intermediate, which is subsequently hydrogenated to the desired 1,4-butanediol product.

Other investigators have endeavored to convert acrolein into 1,4-butanediol by subjecting acrolein to hydroformylation conditions, the objective being the formation of succinaldehyde as an intermediate product. The results have been unsatisfactory since the main conversion product recovered from acrolein under hydroformylation conditions is propionalehyde.

Other efforts to produce 1,4-butanediol have involved hydroformylation of allyl alcohol to yield 4-hydroxybutanal as an intermediate which is subsequently hydrogenated to 1,4-butanediol. The liquid phase hydroformylation of allyl alcohol in the presence of hydroformylation catalysts such as cobalt carbonyl produces significant quantities of propanal, propanol and 2-methyl-3-hydroxypropanal as by-products, in addition to the desired 4-hydroxybutanal.

In United States Patent Office Defensive Publication 904,021 (Nov. 21, 1972) there is disclosed an improved hydroformylation process for converting unsaturated alcohols into diols. In one embodiment the Publication process involves the hydroformylation of allyl alcohol with rhodium-phosphine complex catalyst to produce a reaction mixture which is subsequently hydrogenated to yield 63 percent 1,4-butanediol and 25 percent 2-methylpropanediol, based on the weight of allyl alcohol charged. For the purposes of economic feasibility, higher conversion yields of 1,4-butanediol from allyl alcohol are imperative for commercial scale operations.

Accordingly, it is an object of the present invention to provide an improved hydroformylation process for converting allyl alcohol into 4-hydroxybutanal.

It is another object of the present invention to provide a process for producing 1,4-butanediol from allyl alcohol.

It is another object of the present invention to provide 4-hydroxybutanal in high yield as an intermediate product in a commercially feasible process for converting acrolein into 1,4-butanediol.

It is a further object of the present invention to provide a method for converting allyl alcohol into tetrahydrofuran.

Other objects and advantages shall become apparent from the accompanying description and examples.

DESCRIPTION OF THE INVENTION

One or more objects of the present invention are accomplished by the provision of a process for producing 4-hydroxybutanal which comprises contacting hydrogen and carbon monoxide under hydroformylation conditions with allyl alcohol at a temperature between about 20° C and 120° C and a pressure between about 15 and 150 psi in the presence of hydroformylation catalyst comprising a complex of rhodium metal and phosphine ligand.

HYDROFORMYLATION CATALYSTS

For the purposes of the present invention it has been found that superior results are achieved if the hydroformylation reaction is conducted in the presence of a catalyst which is a complex of rhodium metal and a phosphine ligand.

Any of the rhodium-phosphine complexes disclosed in "Carbon Monoxide in Organic Synthesis", Falbe, (Springer-Verlag 1970), pages 22–23, may be used. Preferred catalysts have the formula $RhCOH(Q_3P)_3$, $RhCOH[(QO)_3P]_3$, $RhCOCl$ $[(QO)_3P]_2$ and $RhCOCl$ $(Q_3P)_2$ wherein Q is phenyl; alkyl phenyl such as tolyl, xylyl, and the like; cyclohexyl; alkyl substituted cyclohexyl such as methyl, propyl, octyl, and the like; substituted cyclohexyl; and aliphatic radical such as methyl, butyl, octyl, and the like; and mixtures of the foregoing, preferably phenyl.

A particularly important aspect of the present invention process is based on the discovery that an exceptionally high yield of straight chain 4-hydroxybutanal is obtained when the hydroformylation catalyst employed is a complex of rhodium metal, carbon monoxide and triaryl phosphine. Illustrative of this class of catalysts is

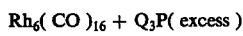

It is to be especially noted that "straight chain selectivity" of product yield is promoted when the molar ratio of triaryl phosphine ligand to rhodium metal in the hydroformylation reaction medium is at least 200 to 1, and preferably at least 400 to 1. Hence, a higher yield of straight chain 4-hydroxybutanal is obtained at the expense of branched chain 2-methyl-3-hydroxypropanal.

HYDROFORMYLATION CONDITIONS

The present invention process for producing 4-hydroxybutanal in high yield selectivity of at least 75 weight percent comprises reacting allyl alcohol with hydrogen and carbon monoxide in the presence of a hydroformylation catalyst as described hereinabove at a temperature between about 20° C and 120° C and a pressure between about 15 and 150 psi. Maintaining the pressure of the hydroformylation system below about 150 psi is an important aspect of the present invention process for achieving conversion of allyl alcohol to 4-hydroxybutanal in high yield selectivity.

Illustrative of a preferred embodiment of the present invention, 4-hydroxybutanal is produced in a yield of at least 87 weight percent by reacting allyl alcohol with hydrogen and carbon monoxide in the presence of rhodium carbonyl-triaryl phosphine complex hydroformylation catalyst at a temperature between 70° C and 110° C and a pressure between about 60 and 100 psi. The relative amounts of hydrogen and carbon monoxide employed can vary in accordance with conventional hydroformylation processes, i.e., a molar ratio between 10:1 and 1:10. It has been observed that a higher yield of 4-hydroxybutanal is favored if the ratio of hydrogen to carbon monoxide in the hydroformylation reaction is maintained in the range between about 2:1 and 1:2.

The hydroformylation catalyst is generally employed in a quantity between about 0.01 and 5 weight percent, based on the weight of allyl alcohol starting material, and preferably a weight percent quantity between about 0.1 and 1.0, exclusive of the weight of ligand.

The hydroformylation reaction of the invention preferably is conducted in a solvent, one which is inert with respect to the products or starting materials. The solvent generally dissolves the catalyst, starting material and products. It is also possible to use the reaction products as the solvent. The latter is a commonly employed industrial expedient. A wide variety or organic solvents such as, for example, aromatics, aliphatics, esters, nitriles, alcohols, halogenated hydrocarbons, and the like, including benzene, cyclohexane, ethyl acetate, methyl alcohol, ethyl orthoformate, tetrahydrofuran, dioxane, isopropyl alcohol, aliphatic hydrocarbon cuts (saturated), chlorobenzene, methylene chloride, propionitrile, acetonitrile, trimethyl acetonitrile, and the like, and mixtures thereof may be employed.

If desired, a hydroxylic organic solvent can be provided as a hydroformylation medium. Such solvents are described in U.S. Pat. No. 3,821,311. "Straight chain selectivity" of product yield is enhanced by the use of hydroxylic organic solvents. Illustrative of such solvents are polyhydric alcohols and etherified polyhydric alcohols having at least one unetherified hydroxyl substituent. These solvents are capable of dissolving the starting materials and the hydroformylation catalyst (e.g., rhodium carbonyl and triaryl phosphine complex).

Polyhydric alcohol solvents which are suitable for use in the present process are desirably polyhydric aliphatic alcohols containing between 2 and about 4 hydroxyl substituents and in which the ratio of the number of carbon atoms to the number of hydroxyl substituents per molecule is between 1 and about 2. Examples of such polyhydric aliphatic alcohols include (but are not limited to) ethylene glycol, 1,2-propylene glycol, 1,3-propylene glycol, 2-methyl-1,3-propanediol, 1,3-butylene glycol, 1,4-butanediol, and the like. Etherified polyhydric alcohols suitable for use according to the present invention are desirably derived from aliphatic alcohols and aliphatic polyhydric alcohols, must have at least one unetherified hydroxyl substituent and desirably contain between 2 and about 4 hydroxyl substituents (including etherified and unetherified hydroxyl substituents) per molecule. It is also a desirable feature of these partially etherified aliphatic polyhydric alcohols that the ratio of the number of carbon atoms to the total number of etherified and unetherified hydroxy substituents per molecule is between 1 and about 2. Examples of such partially etherified polyhydric alcohols include (but are not limited to) ethylene glycol monomethyl ether (i.e., $HOCH_2\text{-}CH_2OCH_3$), diethylene glycol (i.e., $HOCH_2\text{-}CH_2\text{-}O\text{-}CH_2CH_2OH$), diethylene glycol monomethyl ether (i.e., $HOCH_2CH_2\text{-}O\text{-}CH_2CH_2\text{-}OCH_3$), dipropylene glycol (i.e., $HOCH_2\text{-}CH(CH_3)O\text{-}CH(CH_3)\text{-}(CH_2OH)$), 3-methyl-1,3-propanediol monomethyl ether, and the like.

For the operation of the present invention hydroformylation process on a large scale, it is advantageous to employ a rhodium carbonyl catalyst component which is incorporated in a large excess of triaryl phosphine. The said triaryl phosphine can be included in the reaction medium in a quantity which is between 20 and 90 percent of the total weight of catalyst and allyl alcohol reactant. Triphenyl phosphine at a temperature above about 80° C is highly fluid and performs as an excellent medium for the invention hydroformylation process. The highest yields are obtained when triphenyl phosphine is employed as the reaction medium.

Another important advantage of including a solvent as a reaction medium is to insure proper temperature control. Allyl alcohol is highly reactive under hydroformylation conditions, and the solvent performing as a diluent aids in maintaining the reaction rate within controlled limits. It is advantageous to employ a solvent (e.g., triphenyl phosphine or benzene) in a quantity which is at least 50 weight percent of the total reaction mixture, and preferably between about 60–75 weight percent.

The 4-hydroxybutanal which is produced as the high yield product of the invention hydroformylation process can be separated and recovered by conventional distillation procedures. It is highly preferred, however, to subject the hydroformylation product mixture to aqueous phase extraction. Surprisingly it was found that water is capable of extracting 4-hydroxybutanal from the product mixture substantially to the exclusion of the other product mixture components. In a commercial scale operation, an aqueous phase stream can be contacted countercurrently and continuously with reaction product effluent from the hydroformylation reaction zone. The resultant aqueous phase containing 4-hydroxybutanal is an excellent vehicle for subsequent processing procedures, such as hydrogenation of 4-hydroxybutanal with Raney nickel to produce valuable 1,4-butanediol.

UTILITY

The present invention hydroformylation process is a convenient and efficient method for producing 4-hyroxybutanal from allyl alcohol.

4-Hydroxybutanal is an important organic commodity which increasingly finds application as an intermediate for the synthesis of alcohols, ethers, carboxylic acids, resins, and the like.

In another embodiment of this invention, the instant process represents an intermediate synthesis step in the conversion of acrolein into 1,4-butanediol or tetrahydrofuran. For example, a new and efficient method for producing 1,4-butanediol comprises 1. hydrogenating acrolein with a catalyst comprising a solid solution of silver and cadmium metal to form allyl alcohol,
2. converting the allyl alcohol in accordance with the present invention hydroformylation method to 4-hydroxybutanal,
3. hydrogenating the 4-hydroxybutanal to 1,4-butanediol, or optionally,
4. hydrogenating the 4-hydroxybutanal under acidic conditions to yield tetrahydrofuran.

The hydrogenation step (3) can be conveniently accomplished by hydrogenating an aqueous solution of 4-hydroxybutanal employing conventional catalytic procedures. Suitable hydrogenation catalysts include Raney nickel, copper, cobalt, palladium, platinum, and other catalytically active compositions disclosed in literature such as U.S. Pat. No. 3,284,517. The hydrogenation of 4-hydroxybutanal normally can be conducted at a hydrogen pressure of about 1000–4000 psi and a temperature in the range between about 75° C and 200° C.

The hydrogenation and dehydration-cyclization of 4-hydroxybutanal to form tetrahydrofuran in step (4) above is readily accomplished by hydrogenation of 4-hydroxybutanal in an aqueous mineral acid or organic acid medium. Variations of dehydration-cyclicization conditions are described in U.S. Pat. Nos. 3,442,957; 3,726,905; and references cited therein.

The following examples are illustrative of specific embodiments of the present invention process. As it is apparent to those skilled in the art, in the light of the foregoing disclosure numerous modifications are possible in the practice of this invention without departing from the scope or concept thereof.

EXAMPLE I

Conversion of Allyl Alcohol To 4-Hydroxybutanal

Allyl alcohol (10 grams), benzene (40 grams), triphenyl phosphine (30 grams) and hexarhodium hexadecyl carbonyl (0.05 grams) were sealed in a 300 ml "Magnadrive" autoclave. The vessel was pressured with carbon monoxide to 90 psig and depressurized twice then heated to 80° C. A mixture of carbon monoxide and hydrogen (1:1 mole ratio) was admitted to the vessel until the pressure reached 90 psig. Constant gas pressure was maintained on the reaction vessel by means of a pressure regulator attached to a one liter storage vessel also containing a mixture of carbon monoxide and hydrogen (1:1 mole ratio). Gas absorption ceased after 40 minutes. The reactor was cooled to room temperature and the liquid contents analyzed by gas chromatography. The allyl alcohol conversion was found to be 99% to 4-hydroxybutanal (87 wt%), 2-methyl-3-hydroxypropanal (12 wt%) and propanal (1 wt%).

EXAMPLE II

Conversion Of 4-Hydroxybutanal To 1,4-Butanediol

The liquid contents from Example I were extracted with two 25 ml portions of water. A gas chromatograph of the benzene/triphenyl phosphine/rhodium carbonyl showed only traces of aldehydes indicating quantitative extraction of the products by water. These aqueous extracts were combined (59 grams) and hydrogenated with raney nickel (1.0 gram) at 110° C for 2 hours under 1000 psig hydrogen pressure in a "Magnadrive" autoclave. Gas chromatographic analysis of the resulting liquid showed 99% conversion to a mixture of 1,4-butanediol and 2-methyl-1,3-propanediol.

EXAMPLE III

Conversion Of 4-Hydroxybutanal To Tetrahydrofuran

A repeat of the procedure of Example I and Example II was performed except that 5 ml of acetic was added to the aqueous extract before the hydrogenation step. Gas chromatographic analysis again showed 99% conversion of the hydroxy aldehydes to a mixture of tetrahydrofuran, 2-methyl 1,3-propanediol and propanol.

What is claimed is:

1. A process for producing tetrahydrofuran which comprises contacting hydrogen and carbon monoxide under hydroformylation conditions with allyl alcohol in a solvent at a temperature between about 20° C and 120° C and a pressure between about 15 and 150 psi in the presence of a hydroformylation catalyst comprising a complex of rhodium metal, carbon monoxide and triaryl phosphine ligand; recovering the 4-hydroxybutanal from the reaction mixture by aqueous extraction; and subjecting the resultant aqueous extract phase to hydrogenation under acidic conditions to convert 4-hydroxybutanal to tetrahydrofuran.

* * * * *